United States Patent
Redtel

(10) Patent No.: US 12,011,250 B2
(45) Date of Patent: Jun. 18, 2024

(54) DEVICE AND METHOD FOR RECORDING AND ANALYSING IMAGES OF THE SKIN

(71) Applicant: Heiko Redtel, Perleberg (DE)

(72) Inventor: Heiko Redtel, Perleberg (DE)

(*) Notice: Subject to any disclaimer, the term of this patent is extended or adjusted under 35 U.S.C. 154(b) by 812 days.

(21) Appl. No.: 16/982,207

(22) PCT Filed: Mar. 20, 2019

(86) PCT No.: PCT/EP2019/056928
§ 371 (c)(1),
(2) Date: Nov. 24, 2020

(87) PCT Pub. No.: WO2019/180065
PCT Pub. Date: Sep. 26, 2019

(65) Prior Publication Data
US 2021/0068670 A1 Mar. 11, 2021

(30) Foreign Application Priority Data
Mar. 20, 2018 (DE) .......................... 102018002268.5

(51) Int. Cl.
*A61B 5/103* (2006.01)
*A61B 5/00* (2006.01)
(Continued)

(52) U.S. Cl.
CPC .......... *A61B 5/0205* (2013.01); *A61B 5/1032* (2013.01); *A61B 5/441* (2013.01); *G06T 7/0016* (2013.01); *G06T 7/11* (2017.01); *G06T 7/90* (2017.01); *A61B 5/02116* (2013.01); *A61B 5/02125* (2013.01); *G06T 2207/10016* (2013.01); *G06T 2207/10024* (2013.01); *G06T 2207/30076* (2013.01); *G06T 2207/30088* (2013.01)

(58) Field of Classification Search
CPC . G06T 7/11; G06T 7/90; G06T 7/0016; G06T 7/00; A61B 5/1032; A61B 5/441; A61B 5/0205; A61B 5/00; A61B 5/02125; A61B 5/103
See application file for complete search history.

(56) References Cited

U.S. PATENT DOCUMENTS

2013/0109976 A1 5/2013 Farag et al.
2015/0366456 A1 12/2015 Takamori et al.
(Continued)

FOREIGN PATENT DOCUMENTS

WO 2014072461 5/2014

*Primary Examiner* — Tuan H Nguyen
(74) *Attorney, Agent, or Firm* — Sand, Sebolt & Wernow Co., LPA

(57) ABSTRACT

The invention relates to a device and a method for the contact-free analysis of changes to skin color in living organisms, in particular in humans. Images of a skin region to be examined are recorded by means of one or more cameras and are then analyzed, in digital form, by a computer unit. In particular, one or more colors or one or more spectral ranges can be identified in a temporal sequence of occurring intensity changes, and on this basis inferences can be made regarding vital functions, in particular heart rate, pulse wave and the temporal and spatial profile thereof. Data can be derived on this basis which can be used to determine the state of health of the examined individual.

11 Claims, 1 Drawing Sheet

(51) Int. Cl.
*A61B 5/0205* (2006.01)
*G06T 7/00* (2017.01)
*G06T 7/11* (2017.01)
*G06T 7/90* (2017.01)
*A61B 5/021* (2006.01)

(56) References Cited

U.S. PATENT DOCUMENTS

2016/0007865 A1 1/2016 Sakata et al.
2016/0278644 A1* 9/2016 He ........................ A61B 5/7275
2017/0172434 A1 6/2017 Amelard et al.
2017/0354334 A1* 12/2017 Tarassenko .......... A61B 5/0077

* cited by examiner

DEVICE AND METHOD FOR RECORDING AND ANALYSING IMAGES OF THE SKIN

TECHNICAL FIELD

The present invention relates to a device and method for contact-free recording and analysis of images of the skin of a living organism, particularly a human. Changes in skin color can be detected by means of stationary or mobile remote measurement, measurement using a camera, or from an analysis of stationary images or moving images of a living organism, such as a human, obtained by other means. These changes can then be used to make inferences, e.g. regarding the physical performance of the organism. The device and method can particularly be applied for using the data obtained therewith as part of a medical diagnosis and particularly for the early detection of medical conditions.

BACKGROUND

Background Information

Today's camera technology is advanced to the extent that it is by far superior to the human capacity with respect to spatial, color, and temporal resolution as well as with respect to color range. If these advanced properties are applied in a targeted manner and in combination with modern analytic methods, the world can be recognized in a way and represented by facts in an unprecedented manner.

A comprehensive analysis of still images, and even more so of moving images can be helpful and at the same time gentle for a patient in a medical environment.

The advantage of non-contact imaging and its evaluation is the simplicity and also the potential mobility of a respective device, also as the basis for a diagnostic effort to be performed later and targeting such evaluation to detect medical conditions.

1. Theoretical Background

The term skin color designates the coloring of the skin, which inter alia depends on pigmentation, current perfusion, and supply of oxygen.

Medical conditions can alter the skin color as well as the consistent perfusion of the vessels and tissues of a living organism. At the rate of a heartbeat, the pulse pressure waves supply blood to vessels, tissues, and organs, e.g. in humans. Pulsating blood flow through vessels and tissue also generates a temporary change of the skin color at the respective pulse rate.

In a living organism, e.g. in humans, blood supply by a pulse pressure waves follows the principle of physical necessity and the respective structure. Starting from the heart, blood is pumped into the periphery. The arterial branches take the loaded blood into the upper layers of the skin as well. This takes place at every pulse beat.

2. Prior Art

2.1 Status of Moving Image Analysis Techniques

Existing software solutions for the device and method for image analysis of skin images are based on the analysis of color changes using spectral analysis or using the concept of video magnification in which smallest movements are enlarged. An example of such an implementation is the VitalSigns Camera software by Philips.

All prior art systems only determine the pulse rate as a mean value over the entire area of the skin. The frequency of breathing is determined as well, but not separately from the pulse based on the movement of the chest during breathing.

2.2 Status of Camera Technologies

Today's cameras record moving images. A moving image is a sequence of frames, and each frame is a matrix of pixels, each pixel comprising multiple data components or color components.

In today's cameras intended for consumers, each pixel consists of four sub-pixels. Each sub-pixel is a light sensitive area which is covered by a color filter. These color filters typically let the red, green, or blue light pass. Many image data formats store the intensities of these sub-pixels directly a red, green, or blue values.

But there are not only cameras for the range visible to humans. Technically, a much larger range of the electromagnetic spectrum can be imaged. This range ranges from terahertz radiation to X-ray radiation.

2.3 Status of Analysis Techniques for Vascular Diseases

Today's systems, such as the arteriograph by Tensiomed, are used to detect blood pressure and pulse wave velocity. These are used to determine vessel stiffness for detecting vascular diseases. The augmentation index (Aix) provides information about vascular tone (vasolidation) of the small arteries and arterioles. The lower the Aix, the more dilated are the small arteries and arterioles.

A current system by boso simultaneously measures the blood pressure on more than one limb. In addition to blood pressure, PAOD screening using the boso system determines, records, and processes the pulse wave velocities for diagnostic purposes. According to manufacturer information, these two systems currently represent the gold standard in the medical application of non-invasive diagnosis of vascular diseases.

2.4 Status of Analysis Techniques for Skin Changes

Today's uses of Klara (formerly Goderma) enable the analysis of skin changes. These systems can only detect the size of individual nevi or other skin changes and compare it to images taken at a later time.

WO 2014/072461 A1 describes a method and a device for determining vital data such as heart pulse and pulse wave based on recorded images. The disclosed procedure focuses on high-resolution analysis of a locally narrowly restricted area of the skin surface, but it does not provide the option of a highly locally resolved analysis of a large area of the skin surface.

2.5 Extension of Methods Described

The pulse rate and the propagation of the pulse wave can today be determined and represented by means of Doppler sonography. This is locally very restricted examination method in which ultrasound is sent into the tissue. The ultrasound is reflected, inter alia, at the blood cells. Since the blood cells move with the rhythm of the heart, these are sometimes faster and sometimes slower. The reflected ultrasound frequency depends on the velocity of the blood cells and varies minimally with the velocity of the blood cells. This effect is called the Doppler Effect. The velocity of the blood cells can be determined and then graphically represented by analyzing the reflected sound frequency. Doppler sonography is an expensive acquisition and can only be used by trained skilled personnel.

Plethysmography is another system based on the effect of variable skin coloring due to blood flow. Light is radiated into the tissue, typically on a finger, and the reflected light or the light shining through the finger is analyzed. The reflected light or the light shining through the finger shows a variation in brightness with the heart pulse. This method is very sensitive to extraneous light, so a respective arrangement must be enclosed.

3. Summary

The invention is to provide an improved methodology and an improved device compared to prior art systems in order to improve data obtained on color changes of the skin in a non-contact optical measurement of the skin surface of a living organism to be examined, particularly a human, to be able to make additional inferences.

Particularly, it is the object of the invention to present a device and a method which can determine basic data on the cardiovascular system from still images or, preferably, from moving images.

This object is achieved by a device having at least one camera which provides digital image data and a computing device for evaluating the digital image data provided by the at least one camera, wherein the computer unit is adapted and configured to analyze the digital image data in a spatially resolved manner over temporal and/or spatial profiles of skin color changes actually occurring on the skin. Advantageous further developments include that the computer unit may be adapted and configured to analyze the intensity of a color component or a light wavelength of an image in a sequence of images. The computer may further be adapted and configured to analyze the intensity of a color component or a light wavelength of a plurality of images in a sequence of images and to compare them. The computer may further be adapted and configured to divide an image in a sequence of images into tiles and to analyze each of the tiles. The computer may further be adapted and configured to determine the pulse, a pulse wave contour, a pulse wave transit time, a pulse wave velocity, a pulse wave variability, and/or arrhythmias from the obtained data regarding a temporal and/or spatial profile of skin color changes actually occurring on the skin. The computer unit may further be adapted and configured to determine changes of a predetermined skin region over time from the obtained data regarding a temporal and/or spatial profile of skin color changes actually occurring on the skin. The device may further include a display and in that the computer unit may be adapted and configured to graphically output the data determined and analyses performed. The at least one camera may be a camera adapted for recording video sequences. The at least one camera may be a camera adapted for recording frames. The device may comprise two or more cameras directed at different target areas. The device may further be characterized in that it is integrated in a mobile device, e.g., in a smart device having cameras, such as a smartphone, a tablet PC, or the like. The device may further be configured as a stationary unit.

A method achieving the object is characterized in that frames and/or moving images are taken of a skin region to be examined and analyzed in a spatially resolved manner in at least one color and/or one spectral range, preferably in at least two colors and/or spectral ranges, with respect to temporal or spatial intensity changes. Advantageous further developments of this method include that the region to be examined may be selected as being stationary on the skin surface and in that this region may be determined within each image in a sequence of images. The method may further be characterized in that two or more images taken at different times may be placed on top of each other and rotated and pulled in such a manner that the skin region to be examined is identical in both images with respect to size and orientation lying on top of the other. The method may further be characterized in that the at least two images aligned with each other may be compared with respect to the skin region to be examined and may be analyzed with respect to a change of the skin, particularly with respect to size and coloring of skin structures. The method may further be characterized in that intensity changes of the at least one color and/or the at least one spectral range may be captured and evaluated along a straight line in a single image. The method may further be characterized in that intensity changes of the at least one color and/or the at least one spectral range may be captured and evaluated along a plurality of straight lines extending parallel to each other in a single image.

The method may further be characterized in that the skin region to be examined in the at least one image may be divided into tiles, the area of which, compared to the area of the skin region to be examined, is at least smaller such that a plurality of such tiles, particularly at least 20 tiles, may be formed. The method may further be characterized in that a division may be made into tiles having a diameter and/or edge lengths of less than 1 mm. The method may further be characterized in that the location and area of one, multiple, or all tiles on the skin surface may be determined. The method may further be characterized in that the change in intensity of the at least one color and/or the at least one spectral range over time may be determined for each tile and represented in a resulting waveform profile. The method may further be characterized in that the waves of the waveform profile may be normalized and scaled based on the totality of the waves. The method may further be characterized in that the waves in the waveform profile may be examined for local minima and maxima. The method may further be characterized in that the temporal association of the minima and maxima of the various waves may be evaluated with respect to the heart pulse. The method may further be characterized in that the evaluation of the heart pulse may be performed for each heartbeat. The method may further be characterized in that a pulse variability may be determined from the evaluation of the heart pulse for each heartbeat.

The method may further be characterized in that the time difference of associated minima or maxima may be determined for each tile in relation to the minima and maxima of a selected tile, and a pulse wave transit time may be determined therefrom. The method may further be characterized in that the pulse wave velocity may be determined for each tile from the place and pulse wave transit time of that tile. The method may further be characterized in that all waves may be normalized together, particularly to a value of 0% and 100%, and in that this norm may be interpreted as a degree of perfusion of the tissue area under the associated tile. The method may further be characterized in that the amplitude between a local minimum and a chronologically subsequent maximum of the wave of each the may be determined for all minima or maxima. The method may further be characterized in that if tiles are marked in a graphic display of the tiles over an image of the skin surface to be examined based on a limited range for the value of the amplitude between minima and subsequent maxima of the wave of the tiles, such arteries may be displayed in a graphic display which may be characterized by similar diameters and depth under the skin.

The method may further be characterized in that data determined for each tile may be considered two-dimensional data. The method may further be characterized in that a representation of the two-dimensional data as a color or partially transparent marking of an area in the respective tile may depend on the value of the datum assigned to the respective tile on an overlay over an image of the skin region examined. The method may further be characterized in that a type of the data displayed may be set on an overlay. The method may further be characterized in that an overlay may be generated for each freely selectable measuring time, also after a measurement based on stored data. The method may further be characterized in that markings may be introduced into an overlay which point to detected anomalies, particularly to potential medical conditions. The method may further be characterized in that data determined in a display may be correlated using a circular chart, wherein on the one hand there may be a split display with respect to groups of tiles and/or skin regions, and on the other hand a display of individual data in relation to each other may be enabled. The method may further be characterized in that a scale with an indicator may illustrate a relation of values of two groups of tiles to each other, wherein this scale may include markings which characterize a healthy condition, and may include an indicator which displays the condition determined. The method may further be characterized in that images of different skin surface sections may be taken and comparatively analyzed at the same time. The method may further be characterized in that the images may be taken in the range of the infrared spectrum and/or be analyzed for at least one color and/or at least one spectral range of the infrared spectrum.

DETAILED DESCRIPTION

Figure 1:
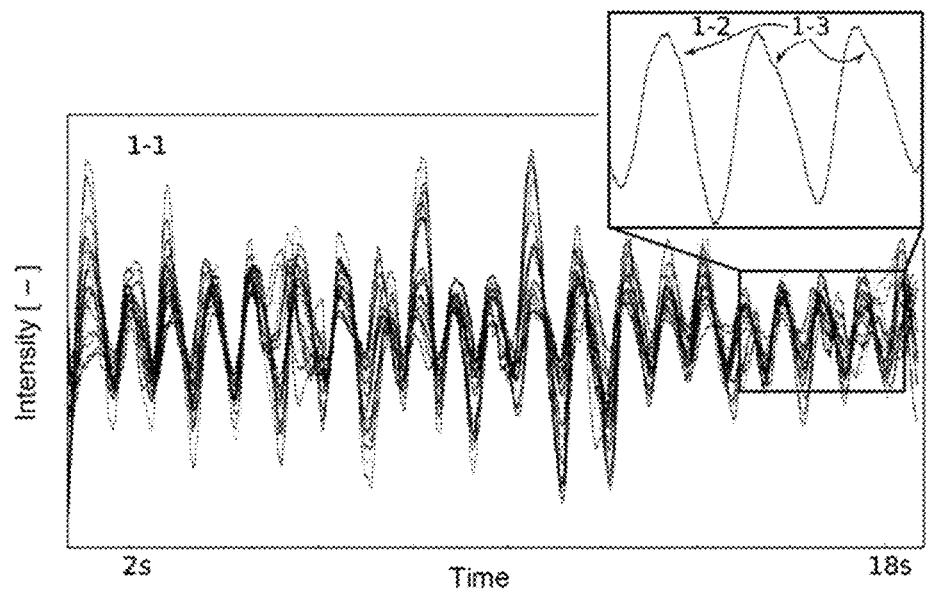
FIG. 1 shows a sample record of color intensity changes in various tiles.

The device and method according to the invention can particularly be used to detect vital data of living beings, particularly humans, based on recorded data on skin color and its change. The device and method presented herein can particularly be used, on the one hand, to accurately determine the heart pulse, locally resolved on the skin surface as well as temporally. On the other hand, the invention also takes the intensity of the color change into account.

The specialty of the invention in this context is that the cardiovascular data obtained from analyzing the skin color can be recorded in a spatially resolved manner. Another specialty of the invention is the option to record the set of different vital data shown simultaneously, the implementation of which is particularly simple and easy. The diagnostic procedures this method allows will be described to highlight the use of this data and the underlying methods and the simultaneous detection of various data.

These advanced options of measuring a living organism, particularly a human, enable far-reaching medically relevant analyses based on the measured values obtained, which analyses are listed in section 4, and the implementation of which is presented in section 6.

This method sets itself apart from the prior art methods for analyzing a moving image with respect to pulse in that a spatially resolved measurement of pulse wave(s) using tiles is made possible. Furthermore, the principle of this measurement is not limited to using light in the range visible to the human eye, but particularly also in other color ranges, e.g. in the infrared range.

These extensions compared to existing technologies particularly allow a deeper assessment of the cardiovascular system of a human based on the data detected. For example, the pulse wave transit time or pulse wave velocity can be determined site-specifically for a body. A difference between a right and a left limb can for example indicate an occlusion of arteries. A difference between the pulse wave velocities of arms and legs can point to beginning occlusions and allow to take timely counteraction.

In addition to this data, data on the course of arteries and veins can be obtained, and further analysis can also lead to statements about the condition of inner organs.

The pulse wave, which is several times faster than the blood itself passes through the arterial bloodstream, causes a change in brightness on the skin surface. This change is not visible to the human eye for a visual diagnostic method. But this change can be detected and measured using a camera with a special resolution and a special frame or image rate per second. Measuring the heart pulse as a frequency is thus possible at every suitable site of the body. The more powerful the camera, the more diagnostic options there are.

The pulse becomes measurable as a simple diagnostic method. The accuracy of pulse measurement is improved depending on the frame rate and its increase. Industrial cameras can take 1000 images per second and more. This allows measurement with medical precision. But a pulse can be measured at a much lower frame rate, and, based on such measurement, peripheral arterial occlusive disease (PAOD) and diabetic foot syndrome (DFS) can be detected, for example.

If pulse measurement is used on different body parts and limbs at the same time, pulse wave velocities become measurable. The pulse wave velocities measured in this manner represent another diagnostic means in comparison.

Medical conditions and stress conditions can be determined from the pulse pressure curve or pulse wave analysis and from pulse wave variability.

For the method according to the invention, the use of a camera which records in the visible and in the infrared ranges is advantageous.

In addition to the color image recording capabilities of a camera, today's cameras intended for consumers sometimes have internal algorithms for improving color. These generate a more beautiful photo for a viewer, but such improvements of color are detrimental to the method according to the invention. Therefore, so-called industrial cameras or cameras for professional video recording are advantageous for use in the method according to the invention.

In addition to color resolution and exact color rendering, the parameters of spatial resolution and temporal resolution or refresh rates are important and should advantageously match the options provided by the best state of the art.

A minimum refresh rate of 300 is needed for detecting the heart pulse over the maximum range to be expected, particularly 25-300 beats per minute, and a required resolution of 5 in the range around 300 beats per minute. Since there is not such a high pulse rate in most cases, cameras with lower refresh rates can be used as well.

The spatial resolution requirements are linked to the use case. If only individual areas of the skin are to be covered, e.g. as part of a medical examination, resolutions in the HD range are sufficient, i.e., 1920×1080 pixels. But if the entire body is to be covered, accordingly higher resolutions are needed.

If HD resolutions and respective lenses are used, not only can one perform a large-area analysis, it is also possible to analyze very small sites. The method does not have to be limited to the analysis of a single small site; multiple such small sites in an area can be covered at the same time. This is advantageous, for example, for detecting malignant moles or for assessing microangiopathy.

A combination of two cameras or one camera with different zoom settings must be used for monitoring tasks, e.g. in public places. One zoom setting tracks the individual to be observed and therefore takes images of the entire individual. The second zoom setting is set to a skin surface area and is trailing the first zoom setting based on the movements determined. Again, only HD resolutions are needed for determining the vital data, but it is structurally advantageous to use higher resolutions due to the weather.

The invention presented here enables improved detection of skin changes even of very small areas due to using selected cameras and logic for detecting color changes. Furthermore, the use of moving images can make other skin changes visible. Hemangiomas, for example, are characterized by an altered perfusion. The invention can be used to make the true size of such hemangiomas visible due to differences in perfusion.

The invention presented herein can particularly replace the above mentioned method of Doppler sonography for tissue parts near the surface and extends that method by a large area under investigation. The equipment for the invention presented here is considerably more cost efficient and can be used by personnel not trained to the extent required for performing Doppler sonography.

Since the invention presented herein works on large areas, brightness variations can be detected and will not lead to measuring errors.

4. Uses

The advantage of the non-contact measurement for diagnosing medical conditions according to the invention is its simplicity and potential mobility. Non-contact diagnosis does not require materials for single use for hygienic operation, eliminating the disposal of such materials for single use. It also eliminates the need for sterilizing multi-use materials. Mobile remote diagnostic measurement/measurement at a distance allows barrier-free working.

4.1 Analysis of the Human Cardiovascular System

The invention detects medical conditions such as peripheral arterial occlusive disease (PAOD) based on a change in skin color. Examples of PAOD are diabetic foot syndrome (DFS), smoker's leg, varicose veins, atherosclerosis, macroangiopathy, or microangiopathy.

These medical conditions manifest themselves in the absence or decrease of the arterial pulse in a tissue region. This can result in death of the tissue and should therefore be detected in time to take effective counteraction.

The invention described analyzes moving image recordings of a skin surface and detects the pulsation of the blood in the tissue. The pulsation is analyzed in comparison to non-diseased tissue parts, which typically are the larger blood vessels. Larger blood vessels also lose less of their visible pulsation due to a potential medical condition and can therefore be used for comparison.

Since the invention described can also perform a locally resolved measurement the pulse can be determined at various sites, particularly simultaneously. Since a high temporal resolution is possible, particularly 300 fps or more, the pulse can be mapped as a wave of changing the intensity of a color at any examined point of the area to be examined.

The wave at a point having a blood flow or non-diseased point has local minima and maxima in sync with the heart pulse. The time difference between two successive maxima or minima yields the RR interval, and the inverse value is the frequency of the heart pulse.

If the frequency of the heart pulse is determined for each heartbeat, the pulse wave variability can be determined as well. It can for example be derived from the standard deviation from the mean value of the determined frequencies of the heart pulse.

The frequency of the heart pulse varies based on physical activities. Therefore, respiration is a major factor at rest. If the frequencies of the heart pulse determined are represented over time in a diagram, the result once again is a wave having local maxima and minima, which are now in sync with breathing, and an analysis of the local minima and maxima yields the respiratory rate.

A temporal offset of the waves relative to each other can be determined when comparing at least two waves at different sites. This temporal offset is the pulse wave transit time between the points, which can also be quantified.

The distance between the at least two points can also be determined in the image. This can approximately be achieved by measuring typical proportions on the body, which will then be used as a scale. These typical proportions are, for example, the distance of the eyes from each other. Markings on the skin can be applied at a known distance from each other for a more accurate generation of the scale. If a scale is known and therefore also the distance between the at least two points, the pulse wave velocity can be determined from the pulse wave transit time. The pulse wave velocity can advantageously be determined for each point of the area to be examined. This is particularly advantageous because the pulse wave velocity depends substantially on two parameters: On the one hand, on the diameter of the arteries, and on the other hand, on the stiffness of the artery walls. Since the size of larger arteries will be visualized in the image, typical pulse wave velocities can be read from a table and compared to the velocity measured. Typical pulse wave velocities, for example for the femoral artery, are at 8-9 m/s in young people.

Excessive pulse wave velocities are a known indicator of vessel stiffness. Local changes of pulse wave velocities, such as side differences, can point to stenoses.

Measuring pulse wave arrival times, starting from each heart action, each individual region of skin areas, reflect the cardiovascular system, such as discrete blood pressure values on arms and legs, the lateral blood pressure difference (e.g. subclavian stenosis), pulse, pulse pressure, arterial pulse contour, venous pressure, venous pulse contour, and indications of any critical heart arrhythmia values.

Furthermore, it is particularly an indication of present medical conditions at respective body or skin regions if no arterial pulse contours or pulse waves are measured.

Peripheral arterial occlusive disease (PAOD) is a macroangiopathy and the result of a progressive atherosclerosis of the leg and foot vessels. Diabetic foot syndrome (DFS) on the other hand is a microangiopathy, which leads to typical changes in foot architecture, tissue perfusion, and protective functions of the foot.

The macroangiopathy underlying PAOD can be treated using revascularizing measures. There is as yet no causal treatment option for the macroangiopathy of DFS. In Germany, currently about 80,000 amputations are performed annually, which go back to these medical conditions. The numbers of amputations are rising annually due to the increase in diabetic diseases.

The procedures and analyses presented so far can be performed by means of conventional cameras using natural light. When using light colors not visible to the human eye and respective cameras, other medically interesting uses can be made possible.

Use of light in two different spectral regions, which is also used in pulse oxymetry, is of interest. The typically used wavelengths are 760 nm and 950 nm. At these wavelengths, the light absorption behavior of hemoglobin depends on oxygen saturation. If a recording is generated in which a color channel is present for both colors, the arteries and veins are visible in both, and subtraction of the one color channel from the other yields an image of the arteries or veins. The following measured values can be determined:
  Local distribution of oxygen saturation in the blood
  Pulse in the arteries
  Pulse in the veins The pulse in the veins is an as yet hardly utilized factor for evaluating the cardiovascular system. The heart suctions blood from the veins during a pulse by means of the atria to press it into the arteries by means of the ventricles in a second phase.

Arterial insufficiency is caused by stenosis in the arteries (atherosclerosis) and results in stiffening of the artery walls, which then leads to an increase in pulse wave velocity compared to a healthy condition.

Venous insufficiency is caused by lasting high blood pressure in the veins (normal value 20-30 mmHg; high pressure values up to 60-90 mmHg). Reasons can be an obstruction of venous drainage or defects on the venous valves. As a result, the veins are dilated. A first and known sign of this are varicose veins. In addition, increased venous pressure leads to destruction of the venous valves, which results in a vicious circle. These conditions are detected by a visible change of the size of the veins and their intensity during a pulse. The more dilated the veins are, the weaker the intensity change compared to a healthy condition.

In the arterial region, the invention fulfills the task of an "arteriosclerosis finder." In the venous return, the invention makes obstructions and occlusions visible. The invention makes the lymph stream visible. The invention determines nerval trophism, such as neuropathy, diabetic microangiopathy, and sweat secretion.

4.2 Analysis of the Human Skin and Tissue

The invention measures skin changes, such as malignant and benign nevi, systemic skin diseases, internal diseases such as icterus, or diseases in the tissue such as cellulitis. The invention can also detect inflammations, e.g. inflammations of the mucous membranes in the mouth, nose, intestine, or genital region.

Detection is based on two backgrounds. The temporal intensity change of the skin color determined is alleviated in the event of skin changes as opposed to the surrounding tissue, which allows detection of the skin changes. In the case of inflammation, the intensity change is typically stronger than in the environment.

The algorithms presented herein can be used in the spatial dimension in addition to the time dimension. Even smallest color changes along a path on the skin can be determined, and two-dimensional color change on the skin surface can be made visible. A combination of measuring the change in color intensity of the skin color over space and time can allow conclusions as to locations in which sweat secretion is elevated. These regions can point to inflammations.

Head's zones are skin areas which were connected to inner organs during embryonic growth and are still connected at full-grown state via the vegetative nervous system. A damaged organ sends out a pain stimulus which is not directly felt at the organ but in the respective zone. This stimulus transmission is called viscerocutaneous reflex. Thus, pain on the right side of the body or in the left arm indicate heart problems. This transmissions of pain stimuli on to the skin surface results in pain-typical responses, e.g. perspiration and/or temperature change. The invention can detect perspiration that has changed compared to the normal state and provide an indication of a problem with an organ. A diagnostic method as yet performed manually, such as thermodiagnosis according to Barrat, can be performed using an automated system with the invention, and physicians who do not have the necessary thermal sensitivity can then use this diagnostic method as well.

An application based on the analysis of moving images to detect a skin change is the precise delineation of a hemangioma (nevus flammeus). Perfusion in such a hemangioma is changed compared to the unchanged tissue. A perfusion analysis provides the exact shape and spread of a hemangioma, which is advantageous for planning and performing cosmetic surgery 4.3 Other Uses in Naturopathy Practice Naturopathy practice uses many diagnostic methods which are based on the analysis of color changes or the effects of which can be assessed by means of detecting color changes. These include, for example:
  Eye diagnosis
  Effect of Kneipp treatments
  Examination of Head's zones In eye and iris diagnosis, it is assumed that the iris changes over one's lifetime due to material, "informational," and psychical environmental influences, nutrition, lifestyle, diseases, their treatment, etc., in that it stores color pigments or locally compresses its fibers.

The invention can be used to visualize a change in color intensity of the iris in a locally resolved manner. The time-resolved intensity change, on the other hand, shows the heart pulse and its detectability on the iris. Both types of information can be analyzed as part of iris diagnosis.

In a Kneipp treatment, so-called hydrotherapies are applied. The body is exposed to cold water, e.g. by treading water. This is meant to enhance the blood circulation and the venous return, for example to alleviate or prevent varicose veins. The invention presents solutions with which both the arterial blood flow and the venous return can be detected.

Use before and after a Kneipp treatment can provide insight into its efficacy. In addition, the size and changes of varicose veins can be detected.

In the case of organic complaints, alternative medical methods try to stimulate Head's zones to achieve an improvement of the inner organs. The success of such treatments can be determined by analyzing their effects.

4.4 Additional Uses

The invention allows determining the perfusion of a tissue from a distance by means of remote measurement. Automated monitoring and evaluation of the variable skin color is a novel method not just in medicine. It is to enable humans to detect medical conditions such as PAOD or DFS early. Therefore the invention can be used preventively, like a thermometer or a blood pressure measuring system, in households of patients and people considered healthy to detect the condition of endangered skin and tissue areas.

In addition to occlusive disease, sport also results in a change of blood circulation. Perfusion increases with moderate sports activities, and in the case of excessive and therefore harmful sports, protective mechanisms of the body reduce perfusion in the outer limbs and cause the formation of cold sweat. Both reactions can be detected. The increase in perfusion at the beginning of a sports activity and its decrease in a break are indicators of the regenerative capacity of an athlete. Regenerative capacity becomes measurable and trainable by the athlete.

Remote measurement of the pulse is an application in itself and can be used in numerous fields. The invention determines the heart rate from heartbeat to heartbeat and can also measure the respiratory rate.

If a person is under stress, the heart pulse is elevated and breathing is flat. The pulse is elevated and breathing is pronounced in moments of joy. The state of mind can be useful in numerous applications:

Video games
Monitoring, e.g. security checks at the airport
Telemedicine
TV shows, e.g. talk shows
Attention monitoring, e.g. in cargo and passenger transport
Quality feedback of a service, such as detection of a state of mind before and after visiting a recreational facility
Detecting the effect of an advertising message Of course, all uses cannot just be applied to humans, but in principle to all vertebrae having a blood circulation. Examples are the medical monitoring of expensive race horses or the detection of stress-free slaughtering of production animals.

5. Technical Implementation

The invention uses a special device and method to make slightest brightness or color changes within an image, a moving image, a time lapse sequence, or a frame sequence visible and quantifiable.

The term "color," as used herein, has a wider meaning than the conventional understanding. In addition to colors that can be perceived by the human eye, there are other light colors which are physically described by a wavelength. Electromagnetic waves or colors having wavelengths from the millimeter range (terahertz radiation), followed by the infrared range, the range of visible light, the UV range, to the picometer range (X-ray radiation) can be recorded as images by means of a technical device today.

Light wavelengths in the visible and infrared ranges are suitable for detecting the pulsating changes of the skin surface. In the visible range, these are the wavelengths of green and blue-violet light, 380-570 nm. In this range, the pulsating change of the skin surface is visible due to the change in brightness caused by filling the arteries with blood. In the infrared range, particularly in the red to near infrared ranges between 0.7 and 3 µm, the light can penetrate the tissue particularly deeply (1-3 mm). Infrared light can particularly be used to represent arteries and veins. The different absorption behavior of hemoglobin depending on oxygen saturations is utilized here. Non-oxygen saturated hemoglobin has an absorption edge at 760 nm, while oxygen saturated hemoglobin is particularly light absorbing at 950 nm. If an image is taken in these wavelength ranges, the arterial and venous pulses can be captured for comparison and the course of the respective arteries or veins can be represented.

Advantageously, a camera with a broad sensitivity in the infrared range can be selected. A camera which also covers the range of 3.5-15 µm can additionally detect thermal radiation and thus detect the temperature and its distribution across the skin.

5.1 Analysis of Moving Images

The invention uses a special device and method for detecting the passing through pulse wave. To this end, moving image recordings of the surface of the skin of a living organism, such as a human, are used.

Starting from the heart, blood is pumped into the periphery. The arterial branches take the loaded blood into the upper layers of the skin as well. This takes place at every pulse beat. The pulse wave, which is several times faster than the blood itself passes through the arterial bloodstream, causes a change in brightness on the skin surface. This change is not visible to the human eye for a visual diagnostic method. But this change can be detected and measured using a camera with a special resolution and a special frame or image rate per second. Measuring the heart pulse as a frequency is thus possible at every suitable site of the body. The more powerful the camera, the more diagnostic options there are.

The pulse becomes measurable as a simple diagnostic method. The accuracy of pulse measurement is improved depending on the frame rate and its increase. Industrial cameras can take 1000 images per second and more. This allows measurement with medical precision. But a pulse can be measured at a much lower frame rate, and, based on such measurement, peripheral arterial occlusive disease (PROD) and diabetic foot syndrome (DFS) can be detected, for example.

A camera designed accordingly and based on the intended application can be used, which camera measures the pulsating change of the skin surface caused by the pulse wave, which is generated starting from the heartbeat.

Depending on the equipment and output of the camera, the entire surface or parts of the skin surface can be measured. In this process, the change in brightness of individual color components or combinations of color components are detected on the respective skin section measured. If pulse measurement is used on different body parts and limbs at the same time, pulse wave velocities become measurable.

This section shows how the pulse wave starting from the heart can be determined from a moving image of an organism, e.g., a human.

The methods presented here are already known in principle, but novel in their compilation and optimization for detecting the pulse wave.

It is advantageous for assessing an organism to determine the pulse wave at one or more fixed locations on the body surface. A resolution as high as possible is an advantage for further analysis. Capturing multiple locations on the body surface simultaneously is a particular novelty and allows far-reaching analyses which are shown in Section 6.

This section will first explain the time-resolved detection of the pulse wave at one location.

The invention can measure and compare individual areas of the skin of a human in a time-resolved manner. But it can also measure color changes of skin cells in a time-resolved manner and compare it to each other skin cell discoloration on the body in a time-resolved manner.

A pulse wave is detected from a moving image as follows:
Detection of the body or body part in the image
Selection of the image segment to be examined
Tracking the image segment in motion Adjusting the size and shape of the image segment during rotation or change of the body position relative to the imaging unit Quantification of the color in the image segment Analysis of the best-suited color in the image segment Analysis of the color change over time for generating the pulse wave Analysis of the pulse wave with respect to intensity, RR interval, respiratory rate, and application specific characteristics Detection of the Body or Body Part in the Image:

Prior art algorithms as provided, for example, in the Open CV library, can be used to detect a human in an image. These algorithms can be adjusted such that they can detect a human or individual body regions, such as the face, in the image.

Selection of the Image Segment to be Examined:

If a pulse measurement is performed on the forehead, the face is found first. The position of the forehead can be found based on fixed proportion from the position of the eyes and the overall size of the face in the image.

If a high resolution is needed, a camera may be used which has to be moved close to the body for said resolution. The image segment on the skin to be captured can be identified by markings on the skin. These can for example be shaped like crosses, which can be detected by many known algorithms.

Tracking the Image Segment in Motion:

For exact detection, the exact area on the skin surface must be examined in every frame of the moving image. When the organism to be examined is moved, the segment in the image moves as well, changing not only its position, but also its size and shape in the image. These changes, even minimal changes, which are present even if a person stands still and cannot be suppressed, must be detected to allow the respective adjustments.

This can be done by repeating the previous steps for each frame. This is not very precise, however, since the detection position and size of the detection algorithms are not always exact, making the tracking inaccurate. In addition, these algorithms require much computing time.

A strategy adapted to this task is to detect individual points which are trackable in the first image. These points must be located on the skin surface near or in the image segment. Known algorithms can be used to find suitable points and to track them.

Adjusting the size and shape of the image segment during rotation or change of the body position relative to the imaging unit The area on the skin can be tracked by tracking points on the skin in the image. Multiple points are tracked, typically at least three. If the positions of the points tracked change in the image, the skin section to be examined has moved in the image as well. Now the size and shape of the image segment representing the skin section to be examined must be changes such that the relations to the tracked points remain the same. This means that, if two points located on two different sides of the skin surface have moved closer to each other, the area along the connecting line of the two points must be compressed to the same extent.

Quantification of the Color in the Image Segment:

The previous section described how a skin section is tracked from frame to frame. A digitally recorded image consists of a plurality of points or pixels. The skin section to be examined extends over a portion of these points. The color in the skin section to be examined is quantified using the mean value of the color. The skin section to be examined typically covers an integral multiple of pixels. The mean value of the color CA over a skin section A is derived from all pixels p of an image as follows:

$$C^\wedge = 1/|A| \Box\_pc(p) \Box(p, A)$$

Wherein |A| is the area of the skin section A, c(p) the color of the pixel p, and $\Box(p, A)$ is a function that outputs a value between 0 and 1, depending on whether the pixel is completely ($\Box(p, A)=1$) or not at all ($\Box(p, A)=0$) contained in A, intermediate values reflecting the areal portion of the pixels in A.

Analysis of the Best-Suited Color in the Image Segment:

The data important for analysis is directly obtained from the color information. In the simplest case, the brightness of the skin section to be examined can be determined and normalized for the image segment.

More meaningful information is obtained if not only an overall brightness is determined but brightness differentiated by colors.

This can be done in two ways. On the one hand, today's common camera models generate a color image by taking the image three times using internal color filters. On the other hand, a color filter specialized for the task can be used to determine medically more meaningful variables. When using a commercially available color camera, the light is filtered, typically by means of color filters for the green, the blue, and the red color components. The sensitive area of a pixel is divided into four sensitive regions or sub-pixels. One respective single region is covered with one of the three color filters. The fourth region is either not sensitive or covered with a green color filter. The use of two regions with a green color filter is reasonable, since the human eye is optimized for the color green.

These three color filters only let the red, the green, or the blue light pass. These colors are sufficient to represent an image that appears colored to a human. These colors can partially be used for the detection of medically relevant variables. The internal color filters are not exactly the same in each camera model, therefore a color component must be selected for detecting the pulse that has the most striking variation in brightness. Therefore the subsequent analyses are performed for all color components, and a time profile of the brightness variation results from the colors accessible to the camera. This time profile is filtered as described below, such that only the time profile of brightness variation due to the heart pulse is visible. A measure of the variation, for example, the standard deviation from the mean value, is determined from these profiles. The profile showing the highest measure for the variation is used for the analysis of vital data.

If the lighting remains similar and the camera used is the same, the color component once found in one human can also be used for other humans.

Cameras by Sony (handycam hdr-sr1 Red Dragon; industrial camera based on an IMX290 sensor) that were examined showed a clear variation in the green color component and a little less variation in the blue color component, whereas the red component showed no variation with the heart pulse. Other camera models (as installed in the Huawei Mate 8 or 9) only showed slight variation in the blue color component. But in a plurality of cameras, first of all, in the consumer sector, no variation can be detected. This is attributed to internal filters for allegedly improved representation.

Analysis of the Color Change Over Time for Generating the Pulse Wave:

The goal of analyzing the color change in the skin section examined is to isolate the color variations with the heart pulse, which are slight relative to the color, such that influences due to movement of the person to be examined or "poor" light can be deducted.

The influences due to movement are already suppressed by tracking the skin section as described above. Examples of influences by "poor" light include: Flickering of lamps for lighting; many lamps flicker depending on the power grid and lamp design; for the power supply common in Germany, this means flickering at 50 or 100 Hz. Sudden changes in brightness; if daylight is used, the movement of clouds can suddenly change brightness; indoors, the movement of people throws shadows. Gradual change in light intensity; when using daylight, light intensity changes with the course of the sun; indoors, the use of lamps, which have to heat up first to reach their full intensity can cause a change in light intensity. Both types of variation, except for the evening and morning hours or directly after switching on lamps, are typically not visible to the human eye, but such a variation is sufficient to cause measurable changes.

The Following Counteraction is Taken Against these Effects:

On the one hand, higher frequencies are removed by digital filters. These can be low-pass filters or running averages. The filters must be adjusted to the frame rate of the camera to attenuate higher frequencies in the signal. Attenuation that is too weak prevents the attenuation of the vibrations due to the power grid, attenuation that is too strong attenuates the signal too much, and fewer details are discernible, such as the reflection wave. It is particularly advantageous to attenuate frequencies greater than 10 Hz. This results in a more noise-free signal.

It is not yet optimal to use the change in brightness for further analysis due to the gradual intensity changes and the one-time sudden changes. The signal must therefore be reduced by its intensity offset. To this end, the (output) signal is filtered a second time using a low-pass filter. A suitable filter is, for example, a Kolmogorov-Zurbenko filter. This filter is a running average applied multiple times. It is adjusted based on the frame rate of the camera, such that smaller frequencies are now attenuated as well. The filtered signal should not include vibrations with the heart rate. Attenuating the smaller frequencies has the effect that sudden changes have an influence over a longer period of time, and attenuation from higher frequencies has the effect that potential changes due to the heart pulse are filtered as well. It is particularly advantageous to attenuate frequencies greater than 0.5 Hz. The signal base results.

The signal, adjusted for interferences at high frequencies and for the signal base, can be obtained by subtracting the signal base from the more noise-free signal. A sample record is shown in FIG. 1, reference numeral 1-1.

If a professional camera is used, particularly one with a frame rate of 300 fps and color dynamics of 24 bit or more, in flicker-free lighting, the adjusted signal can be examined for local minima and maxima. The time and intensity data of the minima and the maxima are thus obtained. A person skilled in the art knows suitable methods for determining local minima and maxima from such a signal.

Analysis of the pulse wave with respect to intensity, RR interval, respiratory rate, and application specific characteristics:

The time interval of two successive minima or maxima is precisely the time a heart pulse takes and is called RR interval. The RR interval can also be expressed as heart pulse, which results from 60s/RR, wherein RR is the RR interval in seconds.

The intensity of the adjusted signal provides two pieces of information. On the one hand, it indicates the perfusion in the skin region observed; for example, a non-variable signal indicates whether an angiopathy is present. If, on the other hand, a variable signal can be detected, the intensity from pulse to pulse can be examined. The intensity profile of the minima and maxima follows the respiration cycle. When inhaling, the blood pressure and thus the filling of the arteries increase, the intensity of the signal decreases, and the intensities of minima and maxima show a shorter distance from each other. When exhaling, this effect is reversed. A waveform signal can be derived from the sequence of the distances of the intensities of successive minima and maxima, the local minima, and maxima of this signal reveal the times of inhaling and exhaling.

The respiratory rate can also be determined in another manner from the adjusted signal. The heart rate increases when inhaling and decreases again when exhaling. The heart rate can be determined from heartbeat to heartbeat, therefore the profile of the heart rate can also be represented over time. This once again results in a waveform signal, and the time intervals of the local minima to the local maxima reveal the times of inhaling and exhaling.

5.2 Analysis of a Frame

The goal of analyzing a frame is to detect smallest color deviations from one skin position to another. Examples of color deviations include moles and other skin changes, see Section 4.2. Every human has a plurality of moles, but most of these moles are not visible to the human eye. The analysis of a frame allows visualizing the moles not visible to the human eye. Further analysis determines the sizes and spatial relations of the moles relative to each other.

The algorithm for detecting these skin changes is similar to the algorithm described above for analyzing moving images. In this algorithm, a point on the skin surface is tracked from frame to frame. Respective pixels are used at a point of the skin. Instead of a fixed point on the skin, the points along a straight line are used in the analysis of a frame. These also comprise a color change, this time not along a time axis but along a space axis. The intensities obtained along the straight line are processed further in the same way as in the previous algorithm for analyzing moving images.

Improved color information can be obtained by using not just one frame but multiple frames taken over a short period of time, e.g., a clip from a video recording. The movement of the depicted body region is determined like in the algorithm for analyzing moving images, and the frames are moved relative to each other and placed on top of each other. A mean value of the color is generated for each point at the points to be examined from the frames placed on top of each other. This reduces color noise and increases the resolution of the intensity change.

The intensity change is not only determined along a straight line, but along a plurality of parallel straight lines, such that the entire area of a skin surface to be examined is covered.

The intensity changes determined can be represented in a two-dimensional view, e.g., as a heat map across an image of the skin section to be examined. Each skin change is visible as an area and clearly distinct from the base.

Known algorithms for blob detection can be applied to the data for adjusting the heat map. These algorithms can be shaped such that the area of the skin changes, their center, their average brightness, and their shape descriptors, such as circular shape, can be determined. The areal and position-related data are determined in pixel or pixel$^2$ units and converted into SI units using a scale. Either typical distances, such as the distance of the eyes from each other, are determined and used as a scale based on typical lengths, or, advantageously, markings are applied to the skin surface and the distance of these markings from each other is used as the scale.

In addition to data on the individual skin changes, data of skin changes and skin abnormalities relative to each other can be determined, which are used in the following description.

5.3 Analysis of Consecutive Frames or Time Lapse Sequences

The analysis of a frame becomes a medical statement if multiple frames of the same skin location are compared to each other. The comparison can reveal the potential growth of a mole in order to remove it before skin cancer develops. To this end, an image of a body location having "suspicious" moles is taken at regular intervals, and the image is analyzed for changes in brightness and color. The time interval between images taken can vary from several days, weekly, to every six months.

The methods listed in the previous section determine the size and position of moles that are visible to the human eye and invisible moles. The goal of analyzing two consecutive images is to detect changes in size of the moles. Under ideal conditions of lighting and orientation of the skin surface to the camera, the determined positions and sizes of the moles (which remain the same from a medical point of view) are identical in the image, and every change in size found is an indication of an endangered mole.

Under realistic conditions, the same lighting and the same orientation of the body to the camera from one image to an image taken later cannot be recreated. However, it is possible to create almost identical conditions. The problem of lighting, as long as lighting is sufficient, plays a subordinate part in the method and is substantially resolved by the methods mentioned in the preceding sections. The problem of a different region between two images is resolved in that the change between the two images is calculated and one image is deformed and rotated such that the deformed and rotated moles (which are unchanged from a medical point of view) match those in the other image.

The problem of adjusting a first image and a second image taken at a later point in time therefore consists of five points:
 The second image shows a region of the skin surface that is rotated compared to the first image.
 The second image shows a region of the skin surface that is greater or smaller compared to the first image.
 The second image shows a region that is spatially tilted compared to the first image.
 The second image shows new moles compared to the first image.
 The second image shows moles with a changed size compared to the first image.

Adjusting two images to each other is achieved using known algorithms of image correlation. These algorithms detect and track points or point patterns in consecutive images and can thus already solve the problems.

After aligning two consecutive images with each other, the sizes of the individual skin changes are determined in both images. Since the two images are aligned, size differences of individual skin changes can be detected or new skin changes become visible. The changes can then be placed as a semi-transparent overlay over a photo of the skin region to be examined, which makes it easy to map endangered skin changes.

6. LOGICS

The invention can measure and compare individual areas of the skin of a human in a time-resolved manner. But it can also measure color changes of skin cells in a time-resolved manner and compare it to each other skin cell discoloration on the body in a time-resolved manner.

The invention measures the pulse wave arrival time at each body location of the skin surface, for example in a human. The plurality of potential data allows significant inferences for a medical diagnosis can for a first time be based on non-contact measuring.

Incoming pulse waves in an overall image of a human reflect the perfusion at each point of the human body in a time and spatially resolved manner.

The invention allows the creation of a tissue and vessel image which provides information about the measuring site and measuring depth depending on the penetration depth of the light. This information can be displayed in a 2 or 3-dimensional depiction of the vessels and the tissue depending on existing computer power.

It was shown in the preceding section (Section 5) how a region of the skin can be analyzed for vital data. Simultaneously analyzing multiple regions of the skin leads to further measurable parameters regarding perfusion of the tissue under the skin.

The regions which a tracked and used for analysis are also referred to as tiles. Advantageously, such tiles are distributed across the skin in the image, such that the entire region is fully covered. Therefore suitable shapes of these tiles are the area-covering shapes of triangle, rectangle, and hexagon. The tiles can also overlap and have other shapes.

The following parameters can be determined by simultaneously analyzing multiple regions:
 Localizing micro and macroangiopathies
 Pulse wave velocity
 Detection of atherosclerosis
 Imaging of the course of arteries and veins Furthermore, the data found is in 2 or 3-dimensional form and difficult to evaluate for a user. Therefore, the following logics are needed for representing, or evaluating and representing, the vital data found:
 Illustration of the pulsation of the arteries relative to each other.
 Showing "suspicious" locations where the tissue under the location may suffer from micro or macroangiopathy or atherosclerosis.
 Propagation of the pulse on the surface of the skin to represent pulse wave velocity.
 Use of the propagation of the pulse for representing the course of arteries and veins.
 A display that represents one-dimensional time-variable data, such as the heart rate, respiratory rate, pulse wave velocity, the time offset of pulsation between two or more locations at one glance and allows evaluation.

6.1 Potential Flow of a Measurement

Depending on the application, either one part or parts of the skin surface or a complete side of a person to be examined are examined. If multiple cameras are used simultaneously, even the entire surface of the body can be examined. The measurement can analyze and represent the data in real time or near-real time. But if a large area of the skin surface is examined, recording, and later analysis are advantageous.

If a large skin region or the entire skin surface is to be examined, two classes of application can be distinguished. On the one hand, the entire area can be captured at once.

This requires a camera with a much higher resolution and the same spatial resolution than for the second class. On the other hand, the skin surface can be examined section by section. If the area is examined section by section, each section has a different time allocation, but a comparatively higher spatial and temporal resolution is made possible, the costs for the system being lower.

The advantage of recording the entire surface using just one camera position is simpler handling of the recording process and use of just one camera without other equipment.

In a section-by-section examination, the advantage is that every section is recorded and then analyzed. A section-by-section examination can be performed with different complexity as follows: On the one hand, the camera can be moved to capture the desired sections. To this end, tripods are placed and aligned for each section. Then the camera is manually moved from tripod to tripod, and a moving image sequence is recorded. The plurality of tripods can for example also be implemented by a vertically oriented board having recesses for the camera for each section to be examined.

But manual alignment of the camera is not advantageous, since it takes a long time and is error-prone. Automated alignment is advantageous. In principle, two methods can be applied. One, the camera can be moved mechanically, two, a system of movable mirrors can be attached in front of the camera, which mirrors can be oriented such that the various skin regions to be examined are mirrored into the camera. Another method is moving the person to be examined.

Mechanical movement is advantageous. It can be implemented, for example, like in an ink jet printer or a fused deposition modeling (FDM) 3D printer. The camera is mounted to a linkage consisting of at least two slide rods. The camera can be moved along these slide rods by means of a moving unit, such as belts or threaded rods. The at least two slide rods are attached to at least two slide rods extending perpendicular to the first at least two slide rods. The first two slide rods plus the moving unit and camera can be moved using another moving unit. This allows exact positioning in an area.

The person to be examined can be moved like in examinations in a MRT device. The person to be examined is fixed on a movable gurney and recorded from the top using a camera. The gurney is now moving step by step and thus, section by section, brings another skin section into the view of the camera.

Today's industrial cameras have very high spatial resolutions and a good temporal resolution. The temporal resolution of these cameras can be increased by limiting the region to be recorded; the limited region is called AOI (area of interest). Thus these cameras are a solution for recording large areas of the skin surface. The AOI is moved section by section, then the respective image is taken.

An important special case is recording two skin sections simultaneously. Of medical interest is a comparison of the right and left body halves or of a body part on the left and a corresponding body part on the right side. For example, the pulse wave transit time between the right and left feet can be observed, wherein the time difference of pulsating color changes due to the heart rate is caused by the fact that the heart is at different distances from the two feet due to the non-central position of the heart in the body. If the two face halves are examined, a time interval of the pulse waves which is offset from normal on both sides can indicate clogging in one of the two skin arteries which lead into the head.

6.2 Localizing Micro and Macroangiopathies

An angiopathy manifests itself by the absence of a pulse in an area of the tissue.

It is made visible by a semi-transparent overlay which is placed over the frames of the moving image timed such that the times of the frames of the moving image match the times of the pulse waves determined. The color or transparency of the overlay in the regions of the tiles is derived from the currently determined intensity of the color change. The overlay over a pulsating artery thus changes color or transparency in sync with the heart pulse. To achieve uniform coloring of the overlay, the intensity variation of each tile must be coordinated with the intensity variations of the other tile. In addition, changes in brightness which affect the entire region must be detected and deducted.

This is achieved as follows: The average height of the local minima and maxima of the intensity variations is determined for each tile at the current time displayed. A mean value is formed from the values of the minima and maxima, preferably a running average. The maxima are processed analogously. The intensity variations are normalized based on the respective mean of the current local minima or maxima and scaled using a color scale or a transparency scale for the overlay. The scaled current value of each tile colorizes the overlay at the current position of the tile over the area of the tile.

Up to this point, the heart pulse is only shown in a spatially resolved manner.

Angiopathies are found by means of an analysis of the normalized intensity variations of the individual tiles. Since these were not normalized for themselves but for all tiles together, the normalized intensity provides information on the strength of perfusion. Normalization can preferably take place as percentage of the running averages of the minima and maxima. The value of the normalized intensity variation thus indicates the level of perfusion. Tiles having an average perfusion of less than 25% over the entire measurement, for example, can be marked by color or transparency in the overlay. The tissue underneath these skin regions could be diseased by an angiopathy and should be further analyzed as part of a more thorough medical examination.

6.3 Pulse Wave Velocity

The pulse wave velocity can be determined from knowing the pulse wave transit time between two points and their distance from each other. The pulse wave transit time becomes visible in a time lapse sequence of the pulse, which is represented by means of an overlay, as shown in the preceding section. Starting from the larger arteries, the perfused area propagates concentrically in the spreading phase of the pulse. Perfusion also vanishes again concentrically.

The pulse wave transit time is detected by graphically representing the intensity variation of the central tile and another tile located in the concentric propagation area. These diagrams are shifted in time relative to each other. The time offset is the pulse wave transit time. The pulse wave transit time can be automatically determined for the intensity variations of each tile. To this end, each intensity variation is examined for local minima and maxima, their times are detected and stored. If a minimum is found in a curve, for example, the pulse wave of the previous beat has already passed through and all previous maxima belong to one beat. The values of the previous maxima are now analyzed and then discarded to enable another measurement. The earliest maximum is found. The associated tile is located on the starting point of the pulse wave. The time differences of the maxima to each other tile determine the pulse wave transit time from the starting tile to the respective tiles.

The location of each tile and the distances to each other tile in SI units must be known to determine the pulse wave velocity. This is achieved by detecting a scale in the image, for example the distance between prominent body features, such as the eyes, or by applying markings to the skin at a known distance.

6.4 Detecting Heart Rhythm Disorder or Arrhythmia

Arrhythmias can be detected by missing or too many heartbeats within the normal heart rate. The average heart rate can be determined because the profile of the heart pulse is also reflected by the color intensity variation within a heart pulse. Since the heart rate can also be determined from beat to beat, an arrhythmia can be detected based on a multiplication of the heart rate (additional beats) or a decrease in heart rate (missing beats).

This feature is not areal and does not necessarily require a two-dimensional analysis. But since optical influences can produce errors in the data, multiple measurements and examining the pulse for multiple tiles is useful to prevent misinterpretations.

6.5 Imaging of the Course of Arteries and Veins

Arteries are represented by analyzing intensity variations. The maximum intensity of intensity variations within an artery is the same as long as the distance to the surface and the diameter of the arteries is the same. The normalized and scaled intensity waves of all tiles are now examined for maximum intensity. Now the tiles which have the same or nearly the same maximum intensity are colorized on an overlay in the same color; the outcome is an image of the arteries.

The veins can be represented in the same manner. It should be noted that the veins cannot be visualized using a conventional camera. As described above in Section 5, a camera in the infrared range and with infrared lighting is required to represent the veins.

6.6 Illustration of the Pulsation of the Arteries Relative to Each Other

After the tiles were allocated to the individual arteries or veins, an overlay can be colorized such that only the pulse in selected arteries is displayed. The artery or vein is selected by selecting or limiting a maximum intensity. An example is the visualization of the two main arteries, which lead into the head, and their pulse differences.

6.7 Joint Representation of all Data Obtained in a Display

Figure 2:
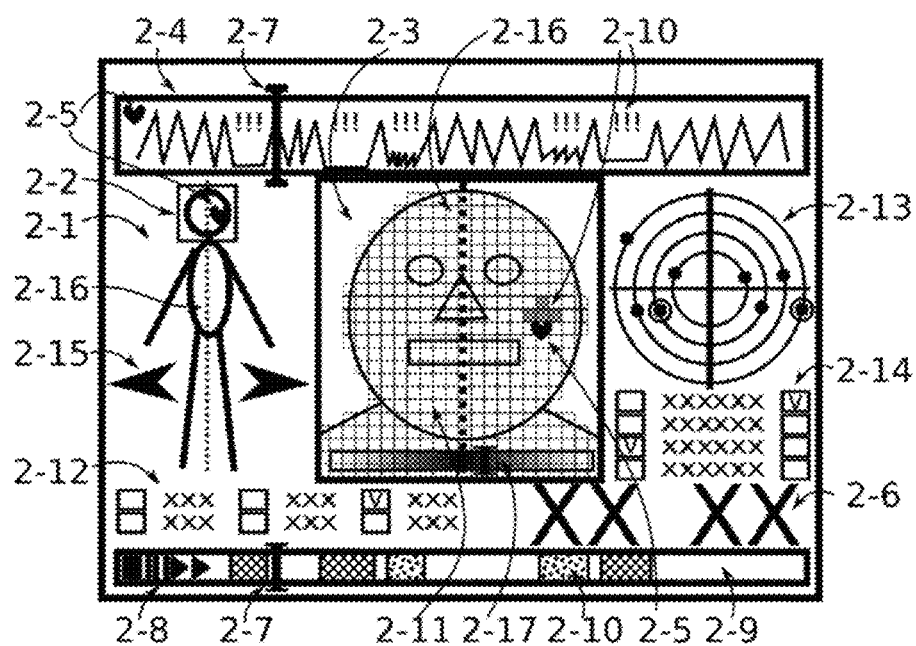
FIG. 2 is an exemplary representation of a graphic interface for illustrating the evaluated data.

A display for illustration of the data obtained and their analysis by a user or by a medically trained person skilled in the art must have the following features; FIG. 2 shows a respective possible design; the reference numerals in parentheses refer to the reference numerals in the figure:

Display of the entire body region captured (2-1);
Selection options for selecting a body region (2-2);
Graphic display of the selected body region (2-3);
Display of the time profile of one-dimensional data (2-4);
Marker and symbol for selecting the position for the time profile of one-dimensional data (2-5);
Display of one or more one-dimensional data for the time currently displayed (2-6);
Selection tool and display of the time to be displayed (2-7);
Setting the playback rate (2-8);
At least one timeline for representing significant events over time (2-9);
Markings for events on the timeline, the size of the markings reflecting the duration and the color fill or manifestation of the fill indicating various phenomena (2-10);
Overlaying the selected body part with a semi-transparent layer which shows a representation of the measured data for each point or each tile and which changes over time as the measured data changes with respect to transparency and/or color at each point or each tile depending on the time profile of the measured data for that point or tile on the skin (2-11);
Selection of the specific examination method (2-12);
Display of all and of a selected set of one-dimensional data at the current time as a circular chart (2-13);
Selection setting for selecting a set of one-dimensional data (2-14);
Setting the section through the data (2-15);
Display of a section through the data as an overlay in the display of the selected body part (2-16);
Display of one or more values obtained for the two sides as an indicator on a scale; this scale can be variably equipped with colors or value markers. Furthermore, an optimum point or normal value or normal value range in healthy users can be introduced to the scale (2-17).

If a measurement is performed, at first an unmanageable plurality of data is available. This data is of two-dimensional nature and advantageously at a high resolution. A display must initially provide an overview, this is shown in FIG. 2, reference numeral 2-1. The entire region measured is schematically represented, in this case a front view of the entire body. A selection tool (2-2) can be used to select the region which is to be displayed in the display (2-3). Place and size can be changed. In addition, a measuring point can be selected (2-5), e.g., at a "suspicious" site, to represent the measured data (2-4) at this point. The value at the current time (2-6) can be selected by a time selector (2-7). Furthermore, playback of moving images can be enabled by known video playback tools (2-8), particularly enabling a time lapse function. Selection of a fixed time or the time of playback results in a display of the real-time image in the display panel (2-3), the current value display (2-6) showing the value at the current time, the circular chart (2-13) representing the selected data (see below), and the two-dimensional data at the selected time being represented as an overlay (2-11).

The overlay (2-11) shows the current value of each tile at the time currently selected, the values being color or transparency-coded, which coding fills the area of the tile. The overlay can also be set in a manner that the individual tiles can be marked, e.g., by a border.

A reduced set of the plurality of data must be displayed to make the representation comprehensible. The setting of the data to be displayed is enabled by selecting (2-12) the examination method and by selecting the data to be displayed (2-14). The selection results in a change of the display of data in the circular chart (2-13). A circular chart consists of concentric circles to which markings are applied which indicate a value depending on the radius. The circular chart is advantageously split to display different values for both body halves. The value of a datum results from the radial position of the marking on the respective circle. Advantageously, a value characterized by a healthy condition of the body is located near the horizontal through the center. An obtained value which characterizes a condition other than healthy will result in the marking moving below or above the horizontal. For example, a heartbeat of 60 beats per minute at rest is a value which characterizes a healthy body. A higher value moves the marking upwards, a lower value downwards. All vital data of the body are interconnected. For the example of the pulse, this means that a pulse of 60 beats per minute is associated with a respiratory rate of 20 to 30 times per minute If this is not measured, the marking of respiration is not in the horizontal. But the optimum range of respiration depends on the heart rate. If the heart rate is elevated, e.g., to 120 beats per minute, an associated value for a healthy respiratory rate is accordingly higher, 50-70 times per minute. Using a circular chart allows displaying different data in relation and also indicates whether the relation of the vital data to each other corresponds to a healthy body condition, and that at one glance.

A timeline (2-9) is present to make abnormalities over time visible at one glance. The timeline shows the current position in time (2-7) and markings (2-19) which point to irregularities. Various types of markings are used on the timeline and in the display elements ((2-3) and (2-4)) to mark various types of abnormalities. In addition to the marking of abnormalities on the timeline, the graphic display of two-dimensional data (2-3) and graphic data (2-4) can be marked as well.

The analysis of differences between the left and right body halves or between two body regions is of medical interest. To this end, a plane (2-16) can be placed through the virtually represented body (2-1) and/or the graphic display of the two-dimensional data (2-3). Selection tools (2-15) can be used to set the position and orientation of the plane (2-16). This plane bisects the raw data and allows the determination of resulting data separately in the two halves to check the halves for differences. A setting therefore also results in changing the data juxtaposed in the circular chart (2-13) and in the display (2-6). In addition, selected data (using 2-14)) can also be juxtaposed in the form of an indicator on a scale (2-17). The position of the indicator shows the side on which the data obtained differ from a healthy state and the degree of the difference. An example is the pulse wave transit time in the face. Due to the two main arteries that lead into the head, both sides of the head are supplied differently, the length of the arteries to the heart is different, resulting in a different pulse wave transit time. The difference in pulse wave transit time between the left and right halves of the head can be displayed. The scale can for example be designed as a color marking from red to green to read, wherein green represents a good and red represents a bad state. The green marking is not central in the case of the pulse wave transit time, but shifted to the right due to the different length of the arteries. This shift symbolizes the typical transit time differences of 3-8 ms. The indicator displays the determined difference in transit time in a relative manner. In this case, a shift of the indicator out of the green range can indicate an occlusive disease in the main arteries, a shift to the right to an occlusion in the right main artery, and a shift to the left to an occlusion in the left artery.

DESCRIPTION OF THE FIGURES

FIG. 1 shows a sample record of color intensity changes in various tiles. Reference numeral 1-1 shows graphs of multiple tiles comprising minima and maxima in sync with the heart pulse. Reference numeral 1-2 shows a graph of a selected tile. Reference numeral 1-3 shows edges in the graph caused by a reflection wave, the pulse wave.

FIG. 2 is an exemplary representation of a graphic interface for illustrating the evaluated data. The graphic interface consists of a plurality of settings which change the display. (2-2) selects the body region to be displayed in a representation of the entire body region (2-1). (2-5) selects a position at which time profiles of one-dimensional data are extracted to display them over time (2-4) and as values (2-6). The type of the time profile of one-dimensional data is determined by the selection of an examination method (2-12) and the selection of a data type (2-14). The data is also displayed in a circular chart (2-13), such that the physical condition at the current time is visible at one glance. In addition to selecting the data, the time (2-7) to be displayed and/or playback of moving images (2-8) can be controlled. The data for the selected or for the current position in the playback are placed as an overlay (2-11) over an image at the time (2-3). Any detected abnormalities are represented as markings (2-10), both in the profile of the one-dimensional data (2-4), in the overlay (2-11), and on a timeline (2-9). In addition to the actual display, a tool for further analysis can be incorporated. The comparison of two body parts with each other is of medical interest; this is made possible by a plane (2-16) which can be arbitrarily selected (2-15). A comparison of the data of the two sides can in addition be illustrated by a scale with indicator (2-17).

The invention claimed is:

1. A method for detection of data in a living organism for use in medical diagnostics, therapeutic support, or cosmetic treatments, comprising:
   taking frames or moving images of a skin region to be examined and analyzed in a spatially resolved manner in at least one color or at least one spectral range with respect to temporal or spatial intensity changes;
   wherein the skin region to be examined in at least one image of the frame or moving image is divided into tiles;
   wherein an area of the tiles which, compared with an area of the skin region to be examined, is at least smaller, such that a plurality of said tiles is formed;
   wherein a change in intensity of the at least one color or the at least one spectral range over time is determined for each tile of the plurality of tiles and is represented in a resulting waveform profile;
   wherein waves in the waveform profile are examined for local minima and maxima;
   wherein a temporal association of the minima and maxima of the waves is evaluated with respect to a heart pulse of the living organism; and
   wherein a pulse variability is determined from the evaluation of the heart pulse for each heartbeat.

2. The method according to claim 1, wherein the skin region to be examined is selected as being stationary on a surface of the skin and the skin region to be examined is determined within each image in a sequence of images.

3. The method according to claim 2, wherein two or more images taken at different times are placed on top of each other and are rotated and pulled in such a manner that the skin region to be examined is identical in the two or more images with respect to size and orientation when lying on top of one another.

4. The method according to claim 3, wherein the two or more images when aligned with each other are compared with respect to the skin region to be examined and are analyzed with respect to a change of the skin, wherein the change of the skin relates to changes in to size and coloring of skin structures.

5. The method according to claim 1, wherein intensity changes of the at least one color or the at least one spectral range are captured and evaluated along a straight line in a single image.

6. The method according to claim 5, wherein intensity changes of the at least one color or the at least one spectral range are captured and evaluated along a plurality of straight lines extending parallel to each other in a single image.

7. The method according to claim 1, wherein a time difference of associated minima or maxima is determined for each tile in relation to the minima and maxima of a selected tile, and a pulse wave transit time is determined therefrom.

8. The method according to claim 7, wherein the pulse wave velocity is determined for each tile from the place and pulse wave transit time of that tile.

9. The method according to claim 1, wherein all waves are normalized together and the norm is interpreted as a degree of perfusion of a tissue area under the associated tile.

10. The method according to claim 1, wherein an amplitude between a local minimum and a chronologically subsequent maximum of the wave of each tile is determined for all minima or maxima.

11. The method according to claim 1 wherein images of different skin surface sections are taken and comparatively analyzed at the same time.

\* \* \* \* \*